United States Patent [19]
Dokkestul et al.

[11] Patent Number: 5,693,361
[45] Date of Patent: Dec. 2, 1997

[54] METHOD FOR FOLIAGE AND OTHER PLANT MATERIAL DYE COLORATION, PRESERVATION AND TOPICAL SEAL COATING

[75] Inventors: Jeffrey L. Dokkestul, Clermont; David L. Hauge, Deltona, both of Fla.; Leo A. Ochrymowycz, Eau Claire, Wis.

[73] Assignee: Preserved Botanicals, Inc., Mount Dora, Fla.

[21] Appl. No.: 666,872

[22] Filed: Jun. 17, 1996

[30] Foreign Application Priority Data

Jan. 5, 1996 [ZA] South Africa ............ 96/0069

[51] Int. Cl.$^6$ ............ A01N 3/00; A01G 5/06
[52] U.S. Cl. ............ 427/4; 427/316; 427/345
[58] Field of Search ............ 427/4, 407.1, 314, 427/316, 345, 296, 430.1; 8/401, 495

[56] References Cited

U.S. PATENT DOCUMENTS

| | | | |
|---|---|---|---|
| 65,777 | 6/1867 | Vining | 427/4 |
| 1,945,148 | 1/1934 | Hughes | 427/4 |
| 3,563,780 | 2/1971 | Waszkiewicz . | |
| 3,573,082 | 3/1971 | Fremling | 427/4 |
| 4,243,693 | 1/1981 | Nordh | 427/4 |
| 4,287,222 | 9/1981 | Robinson . | |
| 4,664,956 | 5/1987 | Dokkestul et al. . | |
| 4,710,394 | 12/1987 | Sellegaard . | |
| 4,788,085 | 11/1988 | DeLuca et al. | 427/4 |
| 4,828,890 | 5/1989 | Tiedeman et al. . | |
| 4,917,922 | 4/1990 | Allison et al. . | |
| 4,980,194 | 12/1990 | Allison et al. . | |
| 5,399,392 | 3/1995 | Sellegaard . | |

*Primary Examiner*—Diana Dudash
*Attorney, Agent, or Firm*—Allen H. Erickson

[57] ABSTRACT

A method for manufacturing long-lasting decorative items from foliage and other natural plant materials by infusion with an aqueous ethylene glycol solution of tartrazine yellow dye, either singly or with co-dye colorants, about 0.1 to 1.6 g/L dissolved $CO_2$ and optional low concentrations of a soluble potassium salt, followed by removal of excess solution and application of a topical water-based organic sealant.

52 Claims, No Drawings

METHOD FOR FOLIAGE AND OTHER PLANT MATERIAL DYE COLORATION, PRESERVATION AND TOPICAL SEAL COATING

BACKGROUND OF THE INVENTION

This invention relates to the treatment of foliage and other plant material to enhance its use as a decoration material. More particularly, the present invention pertains to methods for producing decorative materials from foliage and other plant materials which have long-lasting attractive coloration.

Numerous methods have been cited in the prior art for the systemic plant preservation and concurrent dyeing of plant material by the natural respiration draw of freshly harvested or intact living plants through roots or other plant structures employing a variety of humectant-dye solutions under various environmental conditions. Such methods include the soaking of freshly harvested foliage in humectant-dye vats at atmospheric pressure.

Likewise, some plant materials which lend themselves to initial or eventual preservation by desiccation can be routinely dyed, and even to some degree rehydrated to a full bodied texture, by cold soaking or hot dyeing with or without humectant containing dye solution under various environmental conditions. However, all such methods reported to date suffer limitations in scope, or fail to provide a commercially optimum product due to any of the following limitations:

a. the rendering of the process in practice is limited to only a few select species;
b. the yield of viable product is not uniform and demands extensive culling of viable from non-viable product;
c. the production process is protracted and requires extensive apparatus to treat separated specimen samples so that economy of large undifferentiated batches is difficult to achieve;
d. the preservation process yields products with inadequate shelf-life or display-life;
e. the preservation process does not inhibit fungal or bacterial product deterioration without the use of harsh or toxic and hazardous inhibitors;
f. the dye infusion in the plant material is not uniform; and
g. the dye coloration fades rapidly from chemical and/or photo-induced degradation.

Our present development in this art is in part a modification of our previously described invention, Method for Foliage and Other Plant Material Preservation and Topical Color Application to Same, found in U.S. Pat. No. 4,664,956, issued May 12, 1987. In that disclosure we described the numerous mitigating factors and process specifications to preserve a broad range of foliage and other plant materials and to paint such preserved materials, whereby their aesthetic appearance and extended shelf-life and display-life rendered the end products of great commercial value by sale through the floral trades industry. While we have achieved full commercialization of the preferred embodiments and claims of our prior patent with outstanding floral trades industry acceptance, the specific aesthetic effect of an absolutely natural and lifelike appearance of the preserved and topically coated, i.e. painted, foliage and other plant materials was not claimed nor in practice achieved.

The inherent effects of applying a topical coating colorant of virtually any color, including detailed frosting or shading application of topical coating colorants over an initially applied base colorant coating, which could also serve as the finished product coat, cannot deceive the eye on close inspection.

The preservation process which is described in our U.S. Pat. No. 4,664,956 may be summarized as follows:

A batch of of plant materials is first immersed in a vessel containing a starting volume of aqueous ethylene glycol having a specific gravity of 1.03 to 1.10, and treated at a pressure of about 3–30 psig (about 0.21–2.1 $kg/cm^2$ gauge) for a period of 4 hours to 5 days or more. This range of specific gravity corresponds approximately to 23–77 percent ethylene glycol. The plant fluids are partially exchanged with ethylene glycol, producing treated plant materials containing ethylene glycol solution of specific gravity about 1.025–1.10. The lower value corresponds to a solution containing about 19 percent ethylene glycol.

The treated plant materials are withdrawn from the pressure vessel, i.e. separated from the preservation solution and washed to remove residual ethylene glycol. The plant materials are then dried, and may be topically sealed with a hydrophilic polymeric sealant and optionally topically colored with a pigment.

By its very nature, the preservation process which we earlier developed results in the destruction of the natural chlorophyll green or other natural color of the plant material by a combination of chemical action of the preservative and subsequently by photo-fading to produce a "Buckskin-like" color product. While the Buckskin product has some limited commercial value by virtue of its life-like texture in the preserved state, the lack of natural plant color limits its decorative exploitation. Therefore, the topical application of colorants in the broad variety of formulations previously described and claimed overcomes this limitation in part.

However, the underlying brown, i.e. "Buckskin", appearance of the preserved plant material required application of a high solids content base coat, which imparts an unavoidable, solid hue layer effect to the painted product. Depending on the plant material in question, it was required to apply various degrees of colorant coating to hide the underlying dark tone of the preserved plant material to render an aesthetically pleasing finish.

Thus, for commercial purposes, some species of plant materials incur greater production cost in materials and labor than others, and the production procedures can be highly variable even between lots of a given species of plant material. Any process which overcomes these variable production procedures will yield major commercial advantages.

Moreover, the elimination of the "layer effect" inherent in topical coating would provide the most aesthetically desirable convergence of product appearance with that of the natural, fresh, living state of plant material, which is the ultimate standard of the floral trades industry.

SUMMARY OF THE INVENTION

Accordingly, the basic object of the present invention is to provide a method for dye coloration in concert with preservation of plant material, either freshly harvested or even in the desiccated state, and its subsequent clear coating to enhance its shelf-life, display-life and aesthetic appeal.

In furtherance of the basic object, a further object is to substantially eliminate or significantly reduce the variability in production processes and totally eliminate the layered effect appearance of decorative preserved floral materials.

However, in order to obtain the full advantages of the present invention, the specific advantages offered by our earlier invention in achieving plant material preservation must be retained in their general description as presented in U.S. Pat. No. 4,664,956. In that disclosure, plant materials are immersed in an aqueous mixture of ethylene glycol (specific gravity 1.03–1.10) at a pressure of about 3 to 30 psig for about 4 hours to 5 days, followed by external washing of the plant material.

The critical modification described in this invention is coloration by dyeing of the plant material both concurrently with, and/or after the preservation step previously disclosed. The process comprises pressure infusion through the cell walls of plants and is not dependent upon systemic uptake by freshly cut plants. The process may be utilized with dried plant materials.

A particular yellow dye known as tartrazine yellow is used in combination with other dyes or singly to (a) inhibit dye degradation within the plant, and (b) to provide the desired plant coloration. The dye(s) are used in an aqueous solution of ethylene glycol. Thus, the ethylene glycol solution is both a preservative humectant and a dye carrier. A useful concentration of tartrazine yellow dye has been found to be about 0.03–2.0 percent by weight, with a preferred concentration of about 0.1–0.4 percent. While the minimum concentration required to prevent dye degradation may be small, e.g. about 0.03 percent, higher concentrations may be used as required to obtain the desired color intensity.

Another feature of the invention comprises the addition of potassium ion to the dye solution, resulting in a broader spectrum of plant species amenable to the improved dyeing process. The potassium ion appears to increase the dye infusion into certain plant species. The concentration is not crucial, and may typically be added to the dye solution at an ion concentration of about 0.3–15 g/l. Generally, potassium ion concentrations of 0.6–6.0 g/l are preferred to ensure an adequate degree of dye infusion.

The most critical modification to our U.S. Pat. No. 4,664,956 involves the use of dissolved carbon dioxide in the humectant-dye solutions during the period of infusion. For example, carbon dioxide may be dissolved into the preservation-dyeing solutions while charging the foliage containing pressure vessel with those solutions and the carbon dioxide concentration may be maintained at elevated levels generally throughout the period of humectant-dye penetration at elevated pressure.

While the minimum effective concentration of carbon dioxide has not been unequivocally determined, concentration levels as low as 0.1 g/L have been demonstrated to exhibit a remarkable enhancement in both the absorption rate and the final absorption quantities of humectant and dyes into fresh foliage.

The use of carbon dioxide as an additive in the humectant-dye solutions effectively eliminates the need for potassium ion as a co-agent as described above. However, since potassium ion does not inhibit the effect of carbon dioxide on preservation and dyeing, and in the absence of carbon dioxide additive appears to increase the dye infusion into certain plant species, both carbon dioxide and potassium ion are disclosed as features of this invention. However, in the preferred embodiment, carbon dioxide is not optional, but an essential additive for obtaining the best results, whereas potassium ion is optional.

The surfaces of the products dyed according to this invention may be sealed with a clear-coat barrier film agent. Sealing of the product prevents leakage of dye and humectant, and enhances shelf life and display life.

The present invention circumvents the limitations of prior art processes and achieves a product which is currently far superior, aesthetically, to other products. This is true when the method is applied to freshly harvested, and even when applied to desiccated foliage. Raw material may be uniformly processed at a much higher production rate to produce materials with superior aesthetic and stability properties, as measured by industry standards. Thus, a superior product may be manufactured at a lower unit cost.

Various procedures for making decorative plant products in accordance with the invention are provided in the following description.

DETAILED DESCRIPTION OF THE INVENTION

Nearly two hundred dye combinations were evaluated by an extensive variety of dyeing protocols, and the further combination of a large variety of chemical co-agents. We observed that only a few combinations of dyes and protocols afforded uniform infusion and sufficient depth of dye infusion to temporarily mask the natural brown tone of plant material which resulted from our previously described preferred preservation process with ethylene glycol humectant.

Moreover, we observed that no single dye/co-agent combination was applicable to a broad spectrum of plant species. The scope of plant foliage species which could be sufficiently dyed with uniform dye infusion could be significantly broadened by hot dyeing of previously preserved foliage material in ethylene glycol-dye solutions heated to a temperature as high as 80°–85° C. (176°–185° F.). At higher dyeing temperatures the structure of the preserved foliage materials failed in general to retain long-term structural stability imparted by the usual cold pressure preservation process.

However, with nearly all species of freshly harvested plant foliage material which were pressure preserved and then dyed, by either cold or hot dyeing protocol, color fading in light or dark storage progressively occurred to an unacceptable state well before the display-life structural integrity limit of the preserved material was reached. Thus, the color change of such dyed product rendered the product of little commercial value.

Inclusion of various anti-oxidants, buffers and ultraviolet light blocking agents throughout the process, including various clear coating formulations, failed to remediate the eventual loss of dye coloration. Only when foliage which was first totally desiccated to the dried state, then dyed during our rehydration-pressure preservation protocol could any significant dye coloration be retained for some plant species without significant fading.

It occurred to us that the primary reason why dye degradation may be occurring is because the natural biochemical plant cellular constituents efficiently destroyed the infused dye colorants by a combination of complex direct chemical and/or photochemically coupled processes. Such plant cellular constituents are for the most part likely to be denatured and thus decomposed through foliage desiccation. Such decomposition of the natural biochemical plant cellular constituents likely begins as soon as the foliage is harvested, but takes considerable time under moderate conditions to progress to the terminal state achieved at complete dehydration.

We further rationalized that in the case of systemic draw methods of dye infusion by the natural plant respiration processes, the protracted period of treatment and very extensive water displacement may cause a decomposition of the natural biochemical plant cellular constituents which are involved in dye degradation, similar to denaturing through desiccation; and thus lead to some successful dyeing and preservation results as are occasionally observed.

However, as previously discussed, all such methods as presently practiced produce uneven dye infusion and retention within a bulk sample and require extensive culling of individual specimens which did not achieve sufficient dye infusion before the natural respiration process of the foliage ceased. In such cases the preferred humectant is a mixture of glycerol (glycerin) and water.

Our preference, however, was not to employ glycerol because of its tendency to function as a very effective medium for fungal, yeast and bacterial growth, all of which require inhibition by potent biocides in any viable large scale process. Moreover, the effective unit cost of glycerol greatly exceeds the cost of ethylene glycol, the preferred major constituent in our previously described pressure preservation process. Not only is ethylene glycol comparable to glycerol in preserving plant material by our procedure, but its cost is less, and it also acts as a direct inhibitor of fungal, yeast and bacterial growth. Thus, the use of biocide additives is contraindicated.

Based upon the above experimental observations, we rationalized that we could develop a rapid assay method to evaluate which combination of dyes, with and without potential chemical co-agents, might withstand degradation by undenatured biochemical plant cellular constituents in the presence of ethylene glycol-water concentrations required by our pressure preservation of freshly harvested foliage materials. By several methods we determined that our process produced well preserved foliage materials containing 20% to 55% by weight ethylene glycol of total ethylene glycol-water content of preserved foliage, depending on plant species. We estimate that the fluid of some plant species may contain up to more than about 70% ethylene glycol, after being treated by our process. However, such high concentrations are not necessary for satisfactory preservation.

In our assay method, freshly harvested foliages representative of commercial plant species were placed in a blender with an extraction solvent comprising an aqueous solution containing 40% by weight ethylene glycol. The ratio of fresh foliage to glycol-water extraction solvent was about 0.2 by weight. The mixture was shredded by the blender at room temperature, i.e. 65–75 degrees F., to a fine puree. The resulting puree was vacuum filtered of suspended solids to afford clear extraction solutions containing the dissolved natural plant pigments and other plant cellular materials.

To such solutions were then added various dye combinations, with and without various potential chemical co-agents or buffers which might retard dye degradation, and we observed for dye degradation with time (a) in clear, sealed Pyrex test tubes in the dark, and (b) in a comparative analysis under the influence of intense exposure to broad spectrum artificial ultra-violet light in a photochemical reactor.

To test our rationale, we first heated such foliage extracts at boiling temperature (100° C., 212° F.) to thermally denature the extracted foliage's cellular biochemical constituents, then mixed these preboiled extracts with many different dyes. In confirmation of our reasoning, the result was long term stability of the dyes in the dark. Many dyes also exhibited excellent photostability in such denatured extracts.

Unfortunately, there is no practical thermal denaturing process for intact freshly harvested foliage which could be coupled to our preservation process without completely destroying structural stability of the end product. However, the thermal denaturing assay allowed us to narrow our selection of dyes for further study from those which exhibited stability under both dark and ultraviolet light conditions in the thermally denatured solutions.

When the selected dyes and their chemical co-agent combinants were further assayed in foliage extracts which were not thermally denatured, the list of prospective dye and co-agent combinations dramatically decreased with regard to potential long term stability to degradation both chemically in the dark and photochemically.

Our primary goal was to discover a dye system which would ultimately impart a green coloration approximating the natural green of living foliage. To this end we initially concentrated our assay method on individual green dyes and on blue and yellow dye complements to produce various binary combinations of green coloration. This approach ultimately led us to the critical discovery of the optimum dye formulation which was transferable from our assay method to bulk preservation with concurrent effective dyeing or post-preservation bulk dyeing. This discovery was that essentially no individual blue or individual green dye afforded the desired long term stability to degradation under conditions of our assay method.

However, in combination with a singular yellow dye, such stability could be achieved. This yellow dye is known as Acid Yellow 23, Chemical Abstracts System (CAS) number 1934-21-0, Color Index No.(CI) 19140; it is otherwise known in the dye industry as tartrazine yellow dye, and in highly purified form as the food dye FD & C Yellow, No. 5. This critical agent is not only inherently stable to degradation by the chemical matrix of freshly harvested or dried, then preserved foliage, but also inhibits the degradations of numerous other dyes which lack long term foliage colorant stability in its absence.

In combination with various blue dyes the preferred green hues of natural living foliage were readily achieved upon bulk preservation and dyeing.

Also, in combination with numerous other dye colors, as for example certain red dyes, other stable, exotically colored and preserved foliage materials can be produced. Thus, we have discovered that tartrazine (also known by its various designations as indicated above) functions not only as an acceptable yellow dye colorant, but more critically as an effective inhibitor of biochemical and/or photochemical processes which cause rapid degradation of other dyes infused into foliage with ethylene glycol or glycerol preservative. While the method of this invention is primarily directed at the use of tartrazine yellow dye in an aqueous ethylene glycol solution, a secondary application is its addition to glycerol preservative solutions to permit effective dyeing using glycerol.

However, not all dyes which were complementary to tartrazine in our assay method were suitable for bulk foliage dyeing. Some dyes lacked the minimum requisite chemical/photochemical long term stability even under the stabilizing effect of tartrazine. Other dyes failed to infuse uniformly or sufficiently into foliage concurrently with or after ethylene glycol preservation, or were selectively infused only by distinct species of foliage. In the above tests, broad specimen dyeing of most species of commercially important plant foliages by the ethylene glycol method was found to be restricted to a narrow range of dyes.

In further evaluating the range of plant foliage species for which our general dyeing process is applicable, we observed that the inclusion of a low concentration of potassium ion salts could greatly enhance the degree of dye infusion for some foliage species. The nature of the counter anion of the potassium salt was not critical, such that potassium halides, potassium acetate, potassium sulfate or potassium nitrate afforded the desired effect equally. At the same time, no negative correlation of the essential tartrazine dye infusion to added potassium ion was noted. In fact, for the vast majority of plant species, addition of potassium ion was not essential to achieve appropriate blue or red dye infusion. The effect of added potassium ion was distinctively beneficial for only a relatively select few foliage species, but on no occasion counter-productive for any foliage species. Thus, potassium ion may be uniformly included in our broad spectrum preservation-dyeing formulation at low cost and without any negative effects.

In contemplating the reason that potassium ion may have such a beneficial effect, we turned to the scientific literature regarding plant physiology. According to the literature, the potassium ion concentration is critical in plant respiratory processes and at low levels in living plants helps to sustain high levels of plant respiration. In the numerous methods involving systemic preservation of foliage materials with glycerol solutions, it is almost universally recognized and outlined in patented formulations that potassium ion, usually introduced as potassium nitrate, sustains absorption of glycerol humectant and associated dye materials for a prolonged period of time and thus allows for effective systemic preservation.

Clearly, in the preferred present method, where natural respiratory processes are overwhelmed by highly elevated hypostatic pressure, the effect of potassium ion on respiration may likewise be expected to be insignificant compared to the effect of pressure for most types of plants. Furthermore, where the foliage has been dried, potassium is expected to have no effect at all.

However, for certain foliage types, direct absorption of humectant with associated dyes is clearly aided by potassium ion even under conditions of high pressure.

It is known that living plants exhibit elevated transpiration rates and growth under conditions of elevated carbon dioxide concentration. However, our pressure treatment preservation process is clearly defined by conditions far removed from normal living plant development, and includes the treatment of dried foliage.

We have found that the dissolution of carbon dioxide in the humectant-dye solutions remarkably enhances the rate and extent of humectant and dye infusion. Indeed, the level of humectant absorption by all foliages tested increased, on a weight basis, at least 20 per cent over samples preserved in the absence of carbon dioxide. Furthermore, this enhanced absorption was uniformly achieved in one half or less the infusion time.

Our initial trials were carried out on a small scale whereby solid carbon dioxide (dry ice) was added directly to a small test pressure vessel along with a preservative solution of ethylene glycol, water, tartrazine, potassium ion and various co-dye colorants. Foliage to be preserved was added to the pressure vessel. The vessel was sealed and allowed to increase in pressure from the residual carbon dioxide resulting from dry ice sublimation. The quantity of dry ice added was equivalent to about 0.1 to 1.6 g/l dissolved carbon dioxide. The criteria for evaluating the results was uptake of ethylene glycol and dye(s), as well as the visual appearance of the treated foliage. The foliage treated in this manner uniformly absorbed more ethylene glycol and dye(s), and was visually more pleasing, having uniform coloration to the foliage extremities. We even noted that stems or leaves having insect bites absorbed high concentrations of dye coloration. Without the use of dissolved $CO_2$ in the treatment solution, such foliage dyed poorly at those locations, and often was unsaleable.

Large-scale tests with the $CO_2$-enhanced process were run in a 500 gallon pressure vessel, using product line foliage varieties of Preserved Botanicals, Inc., Casselberry, Fla. These varieties included *sprengeri*, feather fern, Frasier fir, plumosus, black spruce, cedar, boxwood, Maine leather leaf fern, juniper, arbor vitae, tree fern and ming fern. In most cases, mixtures of 4–5 varieties were treated in each batch. Carbon dioxide was added from a storage cylinder and the quantity added was determined by weight. The resulting treated foliage had a greatly reduced quantity of substandard material, increased absorption of ethylene glycol, more intense and uniform dye absorption, and a more pleasing appearance, when compared to preserving/dyeing without added dissolved $CO_2$.

The only aberration we found was that while West Coast cedar was well preserved by this process, a second step of dyeing at elevated temperature was required in accordance with the process described herein to produce a well-dyed product.

There are many ways to produce the dissolved carbon dioxide. For example, dissolved $CO_2$ may be generated in situ by reacting a metal carbonate such as potassium carbonate with an equivalent of a mineral acid. This method is not recommended however, being more expensive and introducing the hazard of handling acids. Also, the metal salt which is produced will require proper disposal. Clearly, the preferred and most direct approach is to charge the preserving or preserving-dyeing solution with gaseous carbon dioxide delivered from a pressurized gas source.

It has been our general observation that the desired effect is produced at dissolved carbon dioxide concentrations of as little as 0.1 g/L in the preservative-dyeing solution. Much higher carbon dioxide levels are tolerated by all of the dyes enumerated subsequently. In general, the acidity of the preserving solutions increased significantly but on no occasion did we observe the pH to fall below 5.3. The pH of the treatment solution, when saturated at standard conditions, was about 5.3, and contained about 1.5–1.6 g/l dissolved $CO_2$. Some dyes are known to exhibit an acid dependent color shift at acidities higher than used in our tests; all those enumerated herein retain their preferred color range throughout the pH range about 7.5–5.3.

The range of plant foliage species to which our general preferred process is applicable includes all those cited in our previous disclosure provided in U.S. Pat. No. 4,664,956, relating to the ethylene glycol pressure preservation process, as follows:

*sprengeri*, plumosus,tree fern; ming fern; plumosus stringers; marsh grass; pepper grass; deer foot moss; Spanish moss; reindeer moss and other mosses; various ferns including leather leaf fern, sword fern, and Florida flat fern; magnolia; palmetto; sparkle berry; *aspidistra*; various huckleberry species; ivies of all types including large ivy, grape ivy, small ivy, and ivies related to the mistletoe varieties; Florida Ruscus; coontie fern; West Coast Huckleberry; West Coast Salal; bear grass; tipi fern; champas; Florida bamboo; all varieties of pines, spruces and firs, including Frasier fir, Austrian pine, Florida shortleaf pine, white pine, black spruce, Hamilton spruce, and hemlocks.

The process described herein may also be usefully applied to the following further list of natural plant material:

| Commercial Name | Species Name |
| --- | --- |
| Mini Oak | *Myrica Guercifolia* |
| Mini Myrtle | *Rafnia Angulata* (Veldtea) |
| Salt and Pepper | Erica |
| Neddle Grass | *Aspalathus Capitata* |
| Large Leaf Eucalyptus | *Eucalyptus Sideroxylon* |
| Tree Fern (Tall) | *Bellreed Sidebranches* |

| | |
| --- | --- |
| Leucadendron | *Leucadendron Platyspurnum* |
| Aspalathus | *Aspalathus Spesie* |
| Heather | Erica - all varieties |
| Leucadendron | *Leucadendron Linifolium* (Tortum) male |
| Wild Eucalyptus | Paranomus |
| Protea Leaves | *Protea Cynaroides* |
| Large Myrtle | *Brunia Neglecta* (Berg Brunia) |
| Cat Tail | *Foxtail SA* |
| Leucadendron | *Leucadendron Linifolium* (Tortum) female |
| Spears | *Watsonia Leaves* |
| | *Phylica Imberbis* |
| | *Euclea Racemosa* (Seeghwarrie) |
| Buxifolium | *Leucospermum Truncatulum* |
| Small Leaf Eucalyptus | *Eucalyptus Lehmannii* |
| Mt. Kol-Kol | *Berzelia Lanuginosa* |
| Mini Holly | Cliffortia |
| Bracken Fern | Bracken Fern |
| Giant Boxwood | *Rhus Tomentosa* |
| Mini Cedar | Elytropappus (Renosterbos) |
| Star Flowers - (Glass Eyes) | *Staavia Radiata* |
| Tree Fern, Short | *Broom Reed, Calopsis Panicullata* |
| Salignum | *Leucadendron Salignum* |
| Pubescens Male | *Leucadendron Pubescens* |
| Boxwood | Rhus |
| Pearl of Africa | *Metalasia Muricata* |
| Salignum Cones | *Leucadendron Xanthoconus* |
| Brunia Clusters | *Brunia Laevis* |

Protea Compacta
Protea Lauicolia
Protea Nerifolia
Protea Repens
Protea Scolymocephala
Leucadendron Laureolum
Leucadendron Tortum male & female
Leucadendron Platyspurnum
Leucadendron Strictum
Leucadendron Sabulosum
Aulax Umbellata
Berzelia Alopecuroides
Berzelia Galpinii
Berzelia Lanuginosa
Brunia Albiflora
Brunia Laevis
Nebelia Paleacea
Retzia Capensis This list is not exhaustive but is merely illustrative of plant species and plant portions to which the method may be applied.

Dyed plant materials can retain dye constituents on their surface or release dye solution to the plant surface through pores over long time periods. Hence, transfer of dyes to other objects upon contact with the plant material may be an unavoidable undesirable property of such products unless inhibited by design.

Accordingly, in one aspect of the invention, the surfaces of preserved and dyed products may be sealed with an efficient clear-coat barrier film agent. Such a coating not only provides a barrier layer to dye transfer, but also enhances product shelf-life and display-life to some degree by providing a sealing barrier to desiccation of the humectant-preserved material. The coating also functions as an infusion barrier against airborne degrading agents such as oxidants (specifically oxygen) or acid-base gaseous agents.

We have found numerous such coating formulations, based on organic or water solvent coating systems of commercial dispersed waxes or polymer latexes, which impart functional clear coat film barriers to preserved-dyed products manufactured in accordance with the present invention.

The preferred clear-coat sealer formulations are water based latexes of the acrylic co-polymer family, such as designated in the trade as Rohm and Haas AC-261 or B. F. Goodrich Chemicals, Hycar-26083 or Carboset GA-1324. Ultraviolet light blocking additives such as are well known in the art may be incorporated in the formulation if desired.

The clear-coat sealant is applied to the surfaces of the preserved and dyed plant material by e.g. dipping or spray coating.

Such coating formulations provide the added aesthetic benefit of the appearance of living plant material, i.e. life-like sheen and feel. Of course, the named sealer formulations are preferred, but other sealants as known in the art may also be used.

The "clear-coat" materials used may produce a finish which is translucent or transparent to light, but preferably the coating is nearly transparent so that the product appears most life-like.

Thus, the dyed end products of our total process are preserved, dyed and clear coated foliage and other plant materials in a broad range of natural and exotic colors of predetermined hues and color intensities, which are offered for sale through the floral trades industry. The display life of our newly manufactured products in floral arrangements, defined as showing essentially no change in structure, texture or color intensity, depend on plant species involved, temperature and relative humidity of the display environment, and the degree of direct exposure to natural or artificial ultraviolet light. For all species described within this invention, such display-life stabilities vary from a minimum of approximately two months in direct, full intensity sunlight at 65°–75° F. and 30% relative humidity (typically the harshest display conditions to be encountered) to indefinitely as display conditions are moderated by lower light and temperature and higher humidity exposure.

1. Preservation, Dyeing and Permanent Retention of Foliage Structure

A preferred process of this invention comprises a method which demands as the first essential consideration the utilization of ethylene glycol preservation humectant in the specific gravity range from 1.10 to as low as 1.03 as specifically described in our previously issued U.S. Pat. No. 4,664,956, except that the use of defoamer agents as described therein is preferably omitted as being unnecessary.

The second essential consideration is the utilization of tartrazine yellow dye, otherwise identified in various systems as Acid Yellow 23, F D & C Yellow No. 5, Chemical Abstract System Number (CAS) 1934-21-0, Color Index Number (CI) 19140. In this process, the tartrazine yellow dye (hereinafter referred to as tartrazine) is used both as a yellow colorant and a chemical/photochemical degradation inhibitor of co-dye colorants. Tartrazine is added to the preferred formulation in dissolved concentrations from about 1 to 3 lbs per 100 gallons of preservation-dyeing solution, i.e. about 0.1 to 0.4 percent by weight.

In producing articles with a color other than that resulting from tartrazine yellow dye alone, a third consideration is the concurrent use of one or more co-dye colorants to impart the desired coloration in combination with tartrazine. Co-dyes which have been found to be compatible with tartrazine in terms of processing and resulting stability are listed below; the list is not intended to be exhaustive, but merely denotes those specific dyes which have been tested and found to be operative in conjunction with tartrazine yellow dye.

Effective Dye Complements to Tartrazine for Foliage Dyeing

| Dye | CAS # | CI # |
|---|---|---|
| Acid Blue 1 (Potent Blue VF) | 129-17-9 | 42045 |
| Acid Green 5 (Light Green SF) | 5141-20-8 | 42095 |
| Food Green 3 (Fast Green FCF) | 2353-45-9 | 42053 |
| Basic Blue 17 (Toluidine Blue O, Tolonium Chloride) | 92-31-9 | 52040 |
| Azure 1 (Azure B) | 531-55-5 | 52010 |
| Direct Blue 1 (Chicago Sky Blue 6B) | 2610-05-1 | 24410 |
| Ingrain Blue 1 (Alcian Blue 8GX) | 33864-99-2 | 74240 |
| Acid Red 52 (Sulforhodamine B) | 3520-42-1 | 45100 |
| Acid Red 94 (Rose Bengal) | 632-69-9 | 45440 |
| Acid Red 18 (New Coccine, Victoria Scarlet 3R) | 2611-82-7 | 16255 |
| Acid Red 73 (Brilliant Croce in Moo) | 5413-75-2 | 27290 |
| Acid Red 92 (Phloxine B) | 18472-87-2 | 45410 |
| Acid Red 183 (Palatine Fast Red GREN) | 6408-31-7 | 18800 |
| Mordant Red 7 (Eriochrome Red B) | 3618-63-1 | 18760 |
| Mordant Red 19 (Metachrome Red 5G) | 1934-24-3 | 18735 |
| Ingrain Yellow 1 (Alcian Yellow) | 61968-76-1 | 12840 |
| Acid Yellow 11 (Flavazin L) | 6359-82-6 | 18820 |
| Acid Yellow 17 | 6359-98-4 | 18965 |
| Acid Yellow 25 (Supramine Yellow R) | 6359-85-9 | 18835 |
| Acid Yellow 29 (Supramine Yellow 3GL) | 6359-91-7 | 18900 |
| Acid Yellow 34 (Fast Light Yellow D3GA) | 6359-90-6 | 18890 |
| Acid Yellow 54 (Palatine Fast Yellow BLN) | 10127-05-6 | 19010 |
| Acid Orange 7 (Orange II) | 633-96-51 | 15510 |
| Acid Orange 10 (Orange G) | 13936-15-8 | 16250 |
| Acid Orange 74 | 10127-27-2 | 18745 |
| Solvent Orange 1 (Sudan Orange G) | 2051-85-6 | 11920 |
| Acid Violet 34 (Alizarin Violet 3R) | 6408-63-5 | 61710 |
| Acid Violet 9 (Violamine R) | 6252-76-2 | 45190 |

A fourth consideration of the invention is the addition of potassium ion equivalent at a dissolved concentration of about 0.2–12.5 pounds potassium ion (about 0.24–15 g/l potassium ion) in the form of inorganic salts to 100 gals of preservation-dyeing solution. The preferred concentration is about 0.6–6 g/l potassium ion. The potassium ion may be added in the form of a soluble inorganic salt such as e.g. potassium acetate or potassium nitrate. The potassium ion concentration appears not to be critical above a minimum value, typically about 0.2 g/l. In addition, the particular counter anion appears not to be critical for effective dye uptake by plant material. Furthermore, most plant species useful for decorative purposes do not require the presence of potassium ion in the humectant solution.

A fifth consideration of this invention is the charging of the preservation solution or preservation-dyeing solution with carbon dioxide to produce dissolved carbonic acid in equilibrium with gaseous carbon dioxide, at a dissolved carbon dioxide concentration of 0.1 g/L up to any concentration as indicated by pH level as low as about 5.3. Typically, the upper pH limit is equivalent to about 15–16 g/l dissolved carbon dioxide.

Dispersion of carbon dioxide into the preserving-dyeing solutions is most effectively achieved by injection of gaseous carbon dioxide into the solutions from a compressed gas cylinder or other source during transfer of the solutions to the preservation-dyeing tanks. Of course, the use of dry ice, or generation of carbon dioxide by chemical reaction may alternatively be used.

The method involves the optional addition of potassium ion in the form of potassium acetate salt (CAS No. 127-08-2) at a concentration of about 4.5 pounds salt per 100 gallons (about 5.4 g/l) of preservation-dyeing humectant solution. The resulting potassium ion concentration is about 2.2 g/l. In general, higher potassium ion concentrations showed no advantage. The advantages afforded by potassium addition are minimal, however, when the preservation solution or preservation-dyeing solution contains an effective concentration of carbon dioxide.

Following are two exemplary preferred one-step formulations of preservation-dyeing solutions. Formulation A renders freshly harvested or structurally intact desiccated (dried) foliage and other plant materials a natural green in appearance color. Formulation B renders the same raw material to be colored red-cranberry in appearance.

Example 1. Formulation A for Green Color One-Step Preservation-Dyeing
Component, Function, and Composition Range:
Ethylene Glycol-Water Solution (Preservative) 100 gal (378.5L) Premixed to 1.07–1.10 Specific Gravity.
Potassium Acetate (Dye Infusion Enhancer) 4.0–4.5 lbs (1.82–2.04 Kg.)
Tartrazine Acid Yellow 23 (Yellow Dye Colorant, Chemical & Photochemical Stabilizer) 1.5–2.0 lbs (0.68–0.91 Kg.)
Patent Blue VF (Acid Blue 1) (Blue Dye Complement) 0.5–0.8 lbs. (0.23–0.36 Kg)

In this formulation, the resulting concentrations of components added to the preservative solution are as follows:

| Ethylene Glycol | 55–77% w/w |
|---|---|
| Potassium acetate (optional) | 4.8–5.4 g/l |
| Tartrazine dye | 1.8–2.4 g/l |
| Patent Blue VF co-dye | 0.6–1.0 g/l |

In the presence of dissolved carbon dioxide, the effect of potassium appears to be negligible or non-existent, at least for the plant varieties which were tested. If the process does not include dissolved carbon dioxide, the potassium ion is required by some plant species to achieve maximum preservation and coloration.

Example 2: Formulation B for Red Color One-Step Preservation-Dyeing
Component, Function and Composition Range:
Ethylene Glycol-Water Solution (Preservative) 100 gallons (378.5 Liters) Premixed to 1.07–1.10 Specific Gravity.
Potassium Acetate (Dye Infusion Enhancer) 4.0–4.5 lbs. (1.81–2.05 Kg.) ( May be omitted for many varieties).

Tartrazine Acid Yellow 23 (Yellow Dye Colorant, Chemical & Photochemical stabilizer) 1.5–2.0 lbs (0.68–0.91 Kg.)

Sulforhodamine B (Acid Red 52) (Red Dye Colorant) 0.5–1.0 lbs. (0.23–0.46 Kg)

The concentration of each component is as follows:

| Ethylene Glycol | 55–77% w/w |
|---|---|
| Potassium Acetate | 4.8–5.4 g/l |
| Tartrazine Acid Yellow Dye | 1.8–2.4 g/l |
| Sulforhodamine B Dye | 0.28–0.56 g/l |

Formulations A and B are intended for a one-step preservation-dyeing process, which may be followed by the clear coating process described below. Preferably, carbon dioxide is dissolved in the formulations at a concentration of 0.1 g/l up to saturation at about 20 degrees C. and atmospheric pressure. At the latter conditions, the concentration of dissolved carbon dioxide is about 1.5–1.6 g/l.

Example 3: Two-Step (Prepreservation and Dyeing) Treatment

The preservation-dyeing procedure can also be carried out in two steps, involving preservation first, followed by a second separate dyeing step. This two-step alternative process offers advantages for the production of a broad range of custom shades and hues of product, particularly in exotic colors. It of course requires the added investment of labor, time and material handling which the one-step process by-passes. Both the one-step and the two-step preservation-dyeing processes exhibit the same essential and initial procedure for the preservation of the foliage. However, if the two-step process is to be exploited, Formulation C is utilized to preserve and stabilize the foliage for the subsequent second dyeing stage of the procedure. The exemplary two-step Formulation C also can serve to produce a product for direct clear coating to yield a pale yellow to yellow-tan color end-product in appearance.

Otherwise, the interim pale yellow to yellow-tan material may be dyed a darker shade and hue of numerous other colors in the second stage by hot or cold dye techniques. The essential consideration of Formulation C is that it includes tartrazine (Acid Yellow 23) and all other constituents as Formulation A and B except the complementary co-dyes as tabulated above. The addition of dissolved carbon dioxide in either or, preferably both of the primary preservation step and the secondary dyeing step produces the most desirable result(s).

Example 4: Formulation C for Yellow-Tan Color One-Step Preservation-Dyeing or Two-Step Predyeing Preservation Component, Function, and Composition Range:

Ethylene Glycol-Water Solution (preservative) 100 gal. (378.5 L.) Premixed to 1.07–1.10 Specific Gravity.

Potassium Acetate (Dye Infusion Enhancer) 4.0–4.5 lbs (1.82–2.04 Kg.). Potassium may be omitted or deferred to the second stage cold dyeing step.

Tartrazine Acid Yellow 23 (Yellow Dye Colorant, Chemical & Photochemical Stabilizer) 1.5–2.0 lbs (0.68–0.91 Kg.)

The exemplary one-step preservation-dyeing or intended two-step preservation-dyeing with Formulation A or B or C then involve the bundling of freshly cut foliage, or desiccated foliage of intact structure, ie. uncurled or unwilted. However, if foliage to be preserved and dyed has been previously desiccated, dye infusion may be inhibited for some foliage types even if uptake of humectant solution appears normal. Moreover, in such cases, carbon dioxide addition appears to have no measurable effect. With respect to all plant types tested, carbon dioxide appears to exhibit its effect as an additive only on fresh, non-desiccated foliage.

The foliage to be preserved and dyed by the process presented herein preferably has not been pre-coated in any way by any other agent. Most specifically, the use of chemical agents such as fungicides or interim topical preservatives is not generally recommended, particularly if applied immediately before harvest or following harvest. Such agents are often utilized to coat foliage in cultured growing operations.

It is usually advantageous to remove any surface contamination by foreign matter, e.g. dust or dirt, adhering to the freshly cut foliage, by brief and gentle washing with cold water, with or without a mild non-ionic detergent of any variety. Residue water from such washing should be allowed to drain from or be shaken gently from the foliage.

In the preferred method, such bundled foliage is placed in a large immersion pressure vessel comprising the preservation-dyeing tank, at up to about three pounds (about 0.7 Kg) of freshly cut foliage, or about 0.5 pound (0.23 Kg) of desiccated, structurally intact foliage, per gallon (3.8 L) of Formulations A, B or C; or like formulations of 1.07–1.10 specific gravity ethylene glycol preservative-dye solution containing 1–3 lbs tartrazine per 100 gal.(1.2–3.6 g/l) of solution. Thus, the amount of foliage may be up to about 185 g/l if fresh and about 60 g/l if desiccated.

The preservation-dyeing solution is typically then added to the pressure vessel, or alternately the converse addition may be employed.

However, in the preferred embodiment, the preservation-dyeing solution is introduced with a strong flow from the bottom center of the vessel by means of a high capacity surge pump from an adjacent reservoir tank. At the juncture where the preservation-dyeing solution enters the pressure vessel, the solution line is fitted with a T adapter which in turn is connected to a high pressure source of compressed carbon dioxide, e.g. a compressed gas cylinder. While the surge pump is transferring solution to the pressure vessel, carbon dioxide is injected into the flow of preservation-dyeing solution. In an exemplary system, carbon dioxide is injected at 20 psig (1.4 Kg/cm$^2$ gauge) pressure and about 4 liters per minute into a stream of preservation-dyeing solution flowing at about 37–45 liters per minute. The strong flow is allowed to fill the tank from the bottom to the top until the solution overflows through a top escape valve and pipeline back to the solution storage tank. At this point, the top escape valve is closed while both the solution surge pump and carbon dioxide injection are continued such that the internal hydrostatic tank pressure in the treatment pressure vessel increases to a high value, e.g. about 30 psig (2.1 Kg/cm$^2$). The pressurized solution may then be allowed to equilibrate for a time, e.g. about 1–2 hours, typically exhibiting a significant drop in pressure. Additional solution may be pumped into the vessel to hydrostatically repressurize to the desired initial value. The total quantity of carbon dioxide introduced into the pressurized solution is deliberately limited to obtain a concentration of dissolved carbon dioxide of about 0.1 to about 1.6 g/l. The preferred concentration is about 0.4 to 1.2 g/l, but concentrations higher than about 1.6 g/l may produce an excessively low pH which changes the dye action. The upper limit of carbon dioxide is of course somewhat dependent upon the water content in the preservation-dyeing solution.

Under these conditions foliage preservation is achieved in as little as four hours for fine structured materials and comprehensively for all foliage types listed in this invention within no more than about 72 hours at room temperature (20°–25° C.).

However, dye infusion is much slower than humectant infusion, and requires typically not less than 12 hours, nor greater than 48 hours, again depending on foliage type, at room temperature. Sprengeri, plumosus, tree fern, and ming are representative of the shorter time range and lower pressure of the preservation-dyeing process; west coast salal, bamboos, firs, spruces, and pines are representative of the longer time and higher pressure ranges of the preservation-dyeing process. In general, the foliage structures which are more heavy bodied and woody require a longer preferred exposure at higher pressure for effective preservation-dyeing in one step. The infusion rate and total absorption are also higher at elevated temperatures.

Effective dyeing is also dependent to a minor degree upon foliage maturity and pretreatment aging. Thus, it is advantageous to design the pressure vessel in such a way that internal pressure can be easily released through the overflow valve and then the batch accessed through a top portal opening for sampling and inspecting the progress of the process on a given batch. With minimal practice, parameters can be quickly established for the optimal pressure and treatment time to achieve predictable color intensity as well as completeness and uniformity of coloration for any particular foliage species at its particular stage of maturity or aged condition since harvest.

Once the particular foliage batch is deemed adequately preserved and dyed, the vessel pressure is reduced to the prevailing atmospheric level, and the preservation-dyeing solution is drained by means of the surge pump in reverse fashion from the bottom of the vessel into the adjacent storage tank. The freshly preserved-dyed foliage is stacked in its bundled form on drain racks (or screens) and excess preservation-dyeing solution is captured below in catch tanks and combined with the recovered solution in the storage tank. Typically, three to five days are adequate for nearly complete drainage of excess solution. In the interim, the foliage is allowed to relax and depressurize, during which time bleed-out of excess infused preservation-dyeing solution is allowed to be achieved. For structurally heavier foliage, longer times will be required for essentially complete bleed-out drainage.

For purposes of solution recovery and convenience of handling, it is acceptable to extend the drainage time indefinitely. However, five days has typically proven feasible for large batches of all species described herein. At this point the relaxed, preserved-dyed foliage is still wet to the touch and covered with excess adhering process solution.

While the preservative composition of ethylene-glycol at specific gravity of 1.10 and below possesses a very high flash point, greatly exceeding that of pure ethylene glycol, the preserved-dyed wet foliage is still combustible. Appropriate restrictions and precautions regarding open flames should be exercised.

Following draining of the foliage, the surface adhesion of the process solution is now removed by moderate washing with cold water and a very small amount of a non-ionic detergent of any variety. The bundles of washed foliage may be shaken free of excess moisture from the water wash and hung to air dry to a state equivalent to that of natural non-wetted foliage. The required time for such drying is dependent on relative humidity, air temperature and air movement. It is advantageous to employ increased air circulation through the drying racked foliage and to maintain temperatures between about 70°–90° F. ( about 21–32 C.). Excessively high drying temperatures may cause some additional bleed-out of preservation-dyeing solution which can largely be avoided by not exceeding 90° F. (32 degrees C.).

Strictly speaking, the dried foliage surface is not free of ethylene glycol. In all cases a thin layer of the humectant and associated dyes remains at the foliage surface through capillary action. However, this small amount of ethylene glycol is tolerated in the next processing stage, i.e. the clear coating process. The effect of the clear coating is to adequately seal the foliage from further bleeding of humectant, moisture and dyes. The clear coat may be either transparent or, to some degree, translucent with respect to light transmission.

While the one-step preservation-dyeing process is of a batch nature, the overall commercial viability of the process requires that the preservation-dyeing solution be reusable through many cycles. During reuse, all constituents of the formulations decrease in concentration by specific infusion into foliage and also due to dilution effects of the displaced foliage cellular water content. While the initial formulation relative to ethylene glycol preservative decreases modestly from a range of 1.10 specific gravity to about 1.04 specific gravity over ten cycles in the process as described, the change in dye and potassium acetate concentration is far more dramatic with each cycle of reuse. Thus, the concentrations of dye(s) and potassium ion in the solution must be supplemented to a greater extent than ethylene glycol.

The overall average recovery of preservative-dyeing solution volume per cycle is 92% plus or minus 1% (loss of 8% plus or minus 1%) at three pounds freshly cut foliage loads per gallon (0.36 kg. per liter) of treatment solution, depending on foliage type. For desiccated (dried) foliage material, the consumption of preservative-dyeing solution is likewise in the range of 5% plus or minus 1% volume per cycle at one-half pound foliage material loads per gallon (0.06 kg. per liter) of treatment solution.

In the meantime, the changes in dye and potassium acetate concentrations decrease approximately proportionately to each other.

It is convenient to monitor dye concentrations spectrophotometrically against a specifically designed calibration curve. However, such precision is not necessary in practice if the following estimates are followed. For both freshly cut and desiccated foliages, the dye concentration has been observed to change almost in linear fashion with a 12±3% decrease for each of the first three cycles. Thereafter, dyeing effectiveness dropped off rapidly. By the completion of the third cycle noticeably less intense and less complete dye infusion results.

Thus, in the preferred embodiment, the decrease in dye concentration should be compensated by proportional dye additions after every two cycles. The same holds true for potassium acetate. Of course, the effect of potassium concentration on dyeing is less noticeable, and may be entirely absent with some plant varieties.

Thus, assuming a 16% volume reduction over two cycles in the working preservation-dyeing solution, and a 25% reduction in dyes and potassium acetate concentration, a superconcentrate of dye and potassium acetate is prepared to fortify lost dye and potassium ion. First, the 25% by weight equivalent of consumed dyes are dissolved with the potassium acetate in a hot water (80° C. or 176° F.) volume equivalent to about 2% of the volume of the original preservation-dyeing solution.

This superconcentrate is added to the bulk solution after each two cycles, followed by an additional makeup 14% volume of ethylene glycol, or as needed to achieve total initial bulk solution volume.

In any case, the proportions of dye and potassium acetate added are in the range of 25% relative to initial weight composition per 100 gallons (378.5 liters) of total solution volume as specified in exemplary Formulations A, B and C.

and the liquid phase make-up volume of water/ethylene glycol is employed in a 1:2 volume ratio to achieve the original total volume of preservative-drying solution. The refortified solution is thoroughly mixed by surge pump recirculation pumping of the solution from the bottom to the top of the storage tank. The mixing of the original preservation-dyeing solutions are achieved in like fashion. Such refortified working solution needs to be monitored for specific gravity.

By the tenth cycle, the specific gravity typically drops to about 1.05±0.01. After the tenth cycle the working solution is considered spent and used no further for fresh cut foliage treatment. The principal reason for not reusing the working solution is that plant cellular extracts become concentrated in the working solution and tend to dull the dye color appearance in the treated foliage. However, ethylene glycol humectant may be recovered by vacuum fractional distillation, such as through the services of a waste reprocessing contractor.

When the reuse cycles are applied exclusively to desiccated foliage material, the number of cycles which may be conducted before the working solution must be sent to solvent recovery may be as many as i.e. 100 or more, and it may even be necessary to add water to maintain the specific gravity of the preservation-dyeing solution below the 1.10 upper preferred limit. In due course, however, plant cellular extracts in the working solution build up and interfere with optimum drying results, likewise requiring reprocessing for ethylene glycol recovery.

As earlier mentioned, Formula C is intended not only to produce a pale yellow to yellow-tan preserved-dyed foliage by a one-step batch process, but also to stabilize foliage for two-step dyeing through preservation and infusion with tartrazine (Acid Yellow 23). Thus, thoroughly preserved and tartrazine-dyed foliage from treatment with Formulation C is treated to the usual cold water wash and air rack drying prior to further dyeing.

While air rack drying can be omitted prior to further dyeing of some foliage species, the most reproducible results with the majority of foliage species are achieved on well dried material.

Moreover, if lighter color shades of dyed product are intended, it is preferable to allow the Formula C derived intermediate product to fade slightly by exposure to direct sunlight or artificial intense ultraviolet light. This typically takes about 60 hours of such exposure. However, during such pretreatment drying and fading, the preserved yellow dyed foliage should not be allowed to dehydrate beyond approximately 25% loss of weight from its freshly preserved dry-to-the-touch stage.

The next step of dyeing can be achieved by several methods. To a significant degree, achievement of a specific shade or hue in these methods is related to artistic judgement and end results depends on unquantifiable considerations.

However, the materials involved in application of such artistic judgement are formulations of commercially available materials utilized to achieve specific aesthetic effects. The most direct method is to simply soak interim Formulation C foliage material at atmospheric pressure in a 1.07 to 1.10 specific gravity ethylene glycol-water-dye solution containing any of the dissolved dyes complementary to Tartrazine as previously tabulated. The shade and hue achieved in combination with the tartrazine yellow background color will be dependent on the secondary dye concentration in this soaking solution, as well as the length of soaking time. In general, this method is functional only after long term, up to two weeks, soaking times to achieve uniform dye penetration. However, for lighter shading effects the method is functional for some species of foliage after two to five days of soaking exposure at moderate dye concentration.

An alternative method is to use similar ethylene glycol-dye solutions and to subject the interim Formulation C material to pressurized redyeing in identical fashion to the one-step processes already described for Formulas A, B and C, except that different dyes and variable concentrations are employed, usually in the absence of any added potassium acetate, but with carbon dioxide treatment, to achieve the aesthetically desired coloration effect. Such pressure redyeing usually decreases the time required for adequate new dye penetration by a factor of two to four over atmospheric pressure soaking. Both of the above methods may be termed room temperature or cold redyeing methods.

The preferred embodiment method for redyeing of interim Formulation C material may be termed a hot redyeing method. In this method, redyeing solutions are prepared as the cold dyeing methods, except that the 1.07–1.10 specific gravity ethylene glycol dye solution is heated to an elevated temperature higher than ambient. Typically, the redyeing solution is maintained between 75°–80° C. (167°–176° F.) in an open dyeing vat fitted with appropriate temperature controls. Alternatively, the temperature may be maintained at any temperature between ambient, e.g. about 10–30 degrees, and about 85 degrees C., depending upon the particular foliage variety.

The interim dry foliage from Formula C treatment is then soaked in the redyeing solution for short periods of time, from about a minute to about an hour, but generally no more than about two hours, depending on foliage species and redyeing solution dye concentration, to achieve the desired aesthetic effect of color shade and hue. Following all such redyeing procedures, the newly redyed, wet foliage is allowed to drain of adhering redyeing solution on a rack or screen to recover the excess redyeing solution, washed, and redried as previously described for the one-step pressure preservation-dyeing method with Formulations A, B and C. Then the redried material is preferably subjected to clearcoat sealing.

It should be noted that specifying a solution of specific gravity 1.07 to 1.10 relates to the initial batch of solution and assumes that the solution may be reused with further lots of foliage until it contains excessive plant fluid constituents. Typically, the specific gravity is then about 1.05. Where the solution is to be used for fewer than 10 cycles, one may start with a solution having a specific gravity lower than 1.07. A starting solution of specific gravity 1.03 may be used for a single batch of foliage, or for several small batches of foliage.

2. Application of Clear Coat Sealing Barrier Film to Preserved-Dyed Foliage.

As previously mentioned, foliage material which is humectant preserved and dyed has the potential to transfer surface adhering dye solution on contact even when apparently dry in appearance and feel. This is particularly true under display conditions of high relative humidity. Indeed the effect is especially acute for dyed foliage preserved by any means with glycerol (glycerine). The use of ethylene glycol in our invention greatly overcomes this undesirable effect.

Never-the-less, to further eliminate the dye transfer potential and to further inhibit bleed-out release of humectant-dye solution, we have devised a clear coat application method to our preserved-dyed foliage materials. While innumerable formulations may be conceived which could be functional in this regard, our formulations and methods of application are conducive to large and rapid scale production by virtue of the specific filming and drying characteristics of our formulations.

The preferred formulations are aqueous dilutions to approximately 10–15% solids of the commercial available acrylic co-polymer latexes available as manufacturer dispersed concentrates of approximately 50% solids. Three specific useful commercial clear coat sealers are Rhom and Haas AC-261 and BF Goodrich Chemicals Hycar-26083 or Carboset GA-1324. After water dilution of any of these latexes to 10–15% solids, a liquid ultraviolet light absorber agent, Tinuvin ® 1130, produced by Ciba-Geigy, is dispersed into the diluted latex at the rate of one fluid ounce per four gallons of the 10–15% solids latex solution. The UV Blocker affords slightly greater long-term color stability to the coated product. The overall clear coat seals, stabilizes and enhances the shelf-life and display-life of our product. These formulations adhere very effectively to the preserved-dyed foliage, dry rapidly, and are not sensitive in their film forming characteristics to residual ethylene glycol on the apparently dry foliage surface.

But most of all, the clear coating most effectively provides a barrier to migration of dye to the foliage surface and essentially eliminates the probability of dye transfer on contact. Other desirable characteristics are that the films do not block during curing and their feel mimics natural living foliages to a high degree relative to alternative formulations.

Our preferred methods of application of the clear coat films are identical to those which we have previously described (by topical dip or air-assisted or airless film application spray gun) in our invention for painting of preserved foliage, U.S. Pat. No. 4,664,956. Thus, the preferred method comprises separating the plant materials from the dye solution, draining the residual dye solution from the plant material, washing with water to remove excess humectant, and air drying. The plant material is then dipped in the clear coat sealer and quickly removed, or the sealer may be sprayed onto the plant material. The sealant dries rapidly, producing an attractive decorative material which retains its natural "feel" for a long time. While the further application of topical colorants, i.e. paints, is not the primary goal of this invention, paints may be topically applied to the preserved and dyed plant materials.

Having described the invention including the presently preferred embodiments, it is understood herein that the invention is defined by the following claims which are to be interpreted in the broadest possible sense in view of the above disclosure.

We claim:

1. A method for preserving natural plant materials having outer surfaces, comprising the steps of:
   infusing said natural plant materials by submersion in an aqueous preservation solution comprising about 23–77 percent by weight ethylene glycol and about 0.1–1.6 g/l dissolved carbon dioxide, for a period of at least one minute; and
   separating said natural plant materials from said preservation solution and removing a major portion of said residual preservation solution from the natural plant material surfaces.

2. The method of claim 1, wherein said infusion step is conducted at a pressure of about 1–2 atmospheres.

3. The method of claim 1, wherein said infusion step is conducted at a temperature between about 10 and 50 degrees C.

4. The method of claim 1, wherein said infusion step is preceded by a drying step to desiccate said natural plant materials.

5. The method of claim 1, wherein said preservation solution contains about 0.3–15 g/l potassium ion.

6. The method of claim 1, wherein said preservation solution further contains about 0.03–2.00 percent by weight tartrazine yellow dye.

7. The method of claim 6, wherein said preservation solution removal step is followed by a step of coating said plant material with a clear coat water based organic sealer.

8. The method of claim 1, wherein said preservation solution is recovered following the plant material removal step and re-used for infusing further natural plant materials.

9. The method of claim 1, comprising the further step of infusing said preserved natural plant materials with an aqueous dyeing solution to dye the surfaces of said materials, said dyeing solution comprising about 23–77 percent by weight ethylene glycol, about 0.03–2.00 percent tartrazine yellow dye, at least one co-dye colorant, and 0.1–1.6 g/l dissolved carbon dioxide.

10. The method of claim 9, wherein said dyeing solution contains 0.3–15 g/l potassium ion.

11. The method of claim 9, wherein said infusion is conducted at a temperature of between about 10 and 85 degrees C.

12. The method of claim 9, wherein said infusion is conducted at a temperature of between about 75 and 85 degrees C.

13. The method of claim 9, wherein said infusion is conducted at a pressure between atmospheric and about 30 psig (2.1 kg/cm$^2$).

14. The method of claim 9, wherein said infusion is conducted for a period of about 1 minute to 2 hours.

15. The method of claim 9, comprising the further step of separating said dyed natural plant materials from said dyeing solution and removing residual dye solution from the surfaces of the materials.

16. The method of claim 15, comprising the further step of coating the surfaces of said plant materials with a clear coat organic water based sealant.

17. The method of claim 9, wherein said at least one co-dye colorant comprises one of Acid Blue 1, Acid Green 5, Food Green 3, Basic Blue 17, Azure 1, Direct Blue 1, Ingrain Blue 1, Acid Red 52, Acid Red 94, Acid Red 18, Acid Red 73, Acid Red 92, Acid Red 183, Mordant Red 7, Mordant Red 19, Ingrain Yellow 1, Acid Yellow 11, Acid Yellow 17, Acid Yellow 25, Acid Yellow 29, Acid Yellow 34, Acid Yellow 54, Acid Orange 7, Acid Orange 10, Acid Orange 74, Solvent Orange 1, Acid Violet 34 and Acid Violet 9.

18. A method for simultaneously preserving and applying colorant to the surfaces of natural plant materials including cut foliage, comprising the steps of:
   infusing said natural plant materials under superatmospheric pressure with an aqueous preservation-dye solution including ethylene glycol, tartrazine yellow dye and dissolved carbon dioxide of at least about 0.1 g/l for a period of at least one minute; and
   removing residual preservation-dye solution from the surfaces of the natural plant materials.

19. The method of claim 18, wherein said preservation-dye solution includes an aqueous mixture of ethylene glycol at specific gravity between about 1.03–1.10.

20. The method of claim 18, wherein said preservation-dye solution contains tartrazine yellow dye at a concentration of about 0.03 to 2.00 percent by weight.

21. The method of claim 18, wherein said preservation-dye solution further contains a co-dye colorant.

22. The method of claim 21, wherein said co-dye colorant(s) comprises at least one of Acid Blue 1, Acid Green 5, Food Green 3, Basic Blue 17, Azure 1, Direct Blue 1, Ingrain Blue 1, Acid Red 52, Acid Red 94, Acid Red 18, Acid Red 73, Acid Red 92, Acid Red 183, Mordant Red 7, Mordant Red 19, Ingrain Yellow 1, Acid Yellow 11, Acid Yellow 17, Acid Yellow 25, Acid Yellow 29, Acid Yellow 34, Acid Yellow 54, Acid Orange 7, Acid Orange 10, Acid Orange 74, Solvent Orange 1, Acid Violet 34 and Acid Violet 9.

23. The method of claim 18, wherein said preservation-dye solution further contains about 0.1 to 1.6 g/l dissolved carbon dioxide.

24. The method of claim 18, wherein said preservation-dye solution contains about 0.3–15 g/l of potassium ion.

25. The method of claim 18, wherein said preservation-dye solution is maintained at a temperature between about 50 and 185 degrees F. (about 10 and 85 degrees C.) while infusing said plant materials.

26. The method of claim 18, wherein said preservation-dye solution is infused at a pressure of up to about 30 psig (2.1 kg/cm² gauge).

27. The method of claim 18, further comprising the step of removing said natural plant materials from said preservation-dyeing solution and removing a major portion of the residual preservation-dyeing solution from the surfaces of said plant materials.

28. The method of claim 18, comprising the further step of coating the surfaces of said dyed plant materials with a clear coat organic water based sealant.

29. The method of claim 18, comprising the further step of recovering and reusing the preservation-dyeing solution to infuse further natural plant materials.

30. A method for preserving natural plant materials having outer surfaces, comprising the steps of:
  infusing said natural plant materials by submersion in an aqueous preservation-dyeing solution comprising about 23–77 percent by weight ethylene glycol and tartrazine yellow dye, for a period of at least one minute; and
  separating said natural plant materials from said preservation-dyeing solution and removing residual preservation-dyeing solution from the natural plant material surfaces.

31. The method of claim 30, wherein said preservation-dyeing solution comprises an aqueous mixture of ethylene glycol at specific gravity between about 1.03–1.10 and tartrazine yellow dye at a concentration of about 0.03–2.00 percent by weight.

32. The method of claim 30, wherein said preservation-dyeing solution contains about 0.3–15 g/l of potassium ion.

33. The method of claim 30, wherein said preservation-dyeing solution is maintained at a temperature between about 50 and 185 degrees F (about 10 and 85 degrees C.) while infusing said plant materials.

34. The method of claim 30, wherein said preservation-dyeing solution is infused at a pressure of up to about 30 psig (2.1 kg/cm² gauge).

35. The method of claim 30, wherein said preservation-dyeing solution contains at least one co-dye colorant in addition to tartrazine yellow dye.

36. The method of claim 30, wherein said at least one co-dye colorant is selected from Acid Blue 1, Acid Green 5, Food Green 3, Basic Blue 17, Azure 1, Direct Blue 1, Ingrain Blue 1, Acid Red 52, Acid Red 94, Acid Red 18, Acid Red 73, Acid Red 92, Acid Red 183, Mordant Red 7, Mordant Red 19, Ingrain Yellow 1, Acid Yellow 11, Acid Yellow 17, Acid Yellow 25, Acid Yellow 29, Acid Yellow 34, Acid Yellow 54, Acid Orange 7, Acid Orange 10, Acid Orange 74, Solvent Orange 1, Acid Violet 34 and Acid Violet 9.

37. The method of claim 30, wherein said infusion step is preceded by a step of drying said natural plant materials.

38. The method of claim 30, wherein said preservation-dyeing solution is recovered and used to infuse additional natural plant materials.

39. The method of claim 30, wherein said process is followed by seal-coating said dyed plant material with a clear-coat water-based organic sealant.

40. A method for preserving and coloring the surfaces of natural plant materials, comprising:
  infusing plant materials in an aqueous preservation solution of ethylene glycol at specific gravity about 1.03 to 1.10 at superatmospheric pressure until substantial exchange of said preserving solution with natural plant fluids results in about 20–55 w/w percent ethylene glycol in the water-ethylene glycol mixture within the plant materials;
  separating said plant materials from the preservation solution and removing excess aqueous preservation solution from the surfaces of said plant materials;
  infusing said plant materials in an aqueous dye solution containing ethylene glycol at specific gravity about 1.03 to 1.10, tartrazine yellow dye, and a co-dye colorant; and
  separating said plant materials from the dye solution and removing residual dye solution from the surfaces of said plant materials.

41. The method of claim 40, comprising the further step of coating the surfaces of the preserved and dyed plant materials with a clear coat water-based organic sealant.

42. The method of claim 40, wherein said aqueous preserving solution contains tartrazine yellow dye at a concentration of about 0.03 to 2.0 percent by weight.

43. The method of claim 40, wherein said aqueous preserving solution contains tartrazine yellow dye at a concentration of about 0.1 to 0.4 percent by weight.

44. The method of claim 40, wherein said aqueous preserving solution contains potassium ion at a concentration of about 0.3 to 15 g/l.

45. The method of claim 40, wherein said at least one co-dye colorant is selected from Acid Blue 1, Acid Green 5, Food Green 3, Basic Blue 17, Azure 1, Direct Blue 1, Ingrain Blue 1, Acid Red 52, Acid Red 94, Acid Red 18, Acid Red 73, Acid Red 92, Acid Red 183, Mordant Red 7, Mordant Red 19, Ingrain Yellow 1, Acid Yellow 11, Acid Yellow 17, Acid Yellow 25, Acid Yellow 29, Acid Yellow 34, Acid Yellow 54, Acid Orange 7, Acid Orange 10, Acid Orange 74, Solvent Orange 1, Acid Violet 34 and Acid Violet 9.

46. The method of claim 40, wherein said dye solution is infused into said plant materials at a temperature of between about 10 and about 85 degrees C.

47. The method of claim 40, wherein said step of infusion with preservation solution is conducted at a pressure of between atmospheric and about 30 psig (2.1 Kg/cm²) for about 4–72 hours at room temperature.

48. The method of claim 40, wherein said step of infusion with said dye solution is conducted at ambient temperature and about atmospheric pressure for a period of up to about two weeks.

49. The method of claim 40, wherein said step of infusion with said dye solution is conducted at ambient temperature and pressure up to about 30 psig (2.1 Kg/cm²) for up to about one week.

50. The method of claim 40, wherein said step of infusion with said dye solution is conducted at a temperature between about 75 degrees and 80 degrees C. at atmospheric pressure for about 1–60 minutes.

51. The method of claim 40, wherein said preservation solution contains between 0.1 and 1.6 g/l dissolved carbon dioxide.

52. The method of claim 40, wherein said step of infusion in an aqueous dye solution containing ethylene glycol includes the introduction of dissolved carbon dioxide into said dye solution at a concentration of between 0.1 g/l and saturation.

* * * * *